United States Patent [19]
Dohi et al.

[11] Patent Number: 5,877,362
[45] Date of Patent: Mar. 2, 1999

[54] METHOD FOR PRODUCING DIPHENYLMETHANE

[75] Inventors: Hideyuki Dohi, Yokohama; Kazuo Sakamoto, Zama; Tadashi Tayanagi, Yokohama, all of Japan

[73] Assignee: Nippon Petrochemicals Company, Limited, Tokyo, Japan

[21] Appl. No.: 925,740

[22] Filed: Sep. 9, 1997

[30] Foreign Application Priority Data

Sep. 12, 1996 [JP] Japan .................................. 8-265520

[51] Int. Cl.$^6$ ............................ C07C 15/12; C07C 15/10
[52] U.S. Cl. ............................ 585/25; 585/6.3; 585/6.6; 585/15; 585/24; 585/400; 585/469
[58] Field of Search ................ 585/6.3, 6.6, 15, 585/24, 25, 400, 469

[56] References Cited

U.S. PATENT DOCUMENTS

| | | |
|---|---|---|
| Re. 29,857 | 12/1978 | Argauer et al. . |
| Re. 32,162 | 5/1986 | Sato et al. . |
| 2,282,327 | 5/1942 | Dreisbach . |
| 3,702,886 | 11/1972 | Argauer et al. . |
| 3,758,403 | 9/1973 | Rosinski et al. . |
| 3,786,107 | 1/1974 | Kuribayashi et al. . |
| 3,790,471 | 2/1974 | Argauer et al. . |
| 3,836,383 | 9/1974 | Kiritani et al. . |
| 3,926,782 | 12/1975 | Plank et al. . |
| 3,936,566 | 2/1976 | Sato et al. . |
| 3,965,209 | 6/1976 | Butter et al. . |
| 4,011,274 | 3/1977 | Wanatabe et al. . |
| 4,035,285 | 7/1977 | Owen et al. . |
| 4,111,825 | 9/1978 | Schulz et al. . |
| 4,117,026 | 9/1978 | Haag et al. . |
| 4,219,687 | 8/1980 | Dolhyj et al. . |
| 4,228,024 | 10/1980 | Schulz et al. . |
| 4,289,806 | 9/1981 | Sato et al. . |
| 4,365,103 | 12/1982 | Chang et al. . |
| 4,454,364 | 6/1984 | Farcasui et al. . |
| 4,463,209 | 7/1984 | Kursewicz et al. . |
| 4,523,044 | 6/1985 | Commandeur et al. . |
| 4,642,730 | 2/1987 | Sato et al. . |
| 4,681,980 | 7/1987 | Sato et al. ................................ 585/6.3 |
| 4,686,548 | 8/1987 | Takahashi et al. . |
| 4,870,221 | 9/1989 | Sato et al. . |
| 4,895,988 | 1/1990 | Clerici et al. . |
| 4,899,009 | 2/1990 | Kawakami et al. . |
| 4,902,841 | 2/1990 | Kawakami et al. . |
| 4,982,025 | 1/1991 | Kawakami . |
| 5,171,906 | 12/1992 | Kawakami et al. . |

FOREIGN PATENT DOCUMENTS

| | | |
|---|---|---|
| 3127905 | 2/1983 | Germany . |
| 46-10064 | 3/1971 | Japan . |
| 1-180835 | 7/1989 | Japan . |

OTHER PUBLICATIONS

J. Chem. Soc. Jpn., Ind. Chem. Sect., 72[7] (1969) pp. 1512–1515 (with English abstract attached) No Month Available Considered as to English Abstract and Statement of Relevence.

*Primary Examiner*—Elizabeth D. Wood
*Attorney, Agent, or Firm*—Fisher, Christen & Sabol

[57] ABSTRACT

A method for producing diphenylmethane from 1,1-diphenylethane with a high yield and selectivity, wherein the 1,1-diphenylethane is reacted with hydrogen and/or water.

16 Claims, No Drawings

METHOD FOR PRODUCING DIPHENYLMETHANE

BACKGROUND OF THE INVENTION

1. Field of the Invention

The present invention relates to a method for producing diphenylmethane which is useful as an intermediate for preparing various chemical compounds.

2. Prior Art

A method for producing diphenylmethane from diphenylethane by heating the latter is described, for example, in J. Chem. Soc. Jpn., Ind. Chem. Sect., 72, [7] (1969), pp 1512–1515. The major reaction products, however, are: (1) benzene and ethylbenzene which are considered to be the reaction products of hydrogenolysis, (2) 1,1-diphenylethylene as the product of dehydrogenation and (3) styrene as the product of the decomposition of diphenyl methane. Meanwhile, the yield of the desired diphenylmethane is very small.

BRIEF SUMMARY OF THE INVENTION

It is, therefore, the object of this invention to provide a method for producing diphenylmethane as a major reaction product from 1,1-diphenylethane with high yield and selectivity.

As a result of the intensive studies, the inventors have found that it is advantageous to react 1,1-diphenylethane with hydrogen and/or water in order to produce diphenylmethane as a major product, thereby accomplishing the present invention.

Accordingly, the first aspect of this invention relates to a method for producing diphenylmethane which is characterized in that 1,1-diphenylethane is reacted with hydrogen and/or water.

The second aspect of this invention relates to a method for producing diphenylmethane which is characterized in that the reaction is carried out according to the first aspect of this invention in the presence of a metal catalyst and/or metal oxide catalyst.

DETAILED DESCRIPTION OF THE INVENTION

The present invention will now described in more detail.

The starting material used in the method of the present invention is 1,1-diphenylethane. Hydrocarbon materials containing more than 50% by weight of 1,1-diphenylethane can also be used as a starting material. It is well known that 1,1-diphenylethane is formed as a by-product in various chemical processes. For example, 1,1-diphenylethane is contained in amounts of as much as 50% by weight or more in the heavy fractions which are obtained as a by-products in the process for producing ethylbenzene by the reaction of benzene with ethylene. The by-product oil of this kind is suitable as a raw material in the method of the present invention.

In the present invention as described above, 1,1-diphenylethane is reacted with hydrogen or water or their mixture. As described in the above-mentioned literature, when 1,1-diphenylethane is used as the only reactant, only a small amount of diphenylmethane is obtained even when a catalyst is used.

It is believed that the reaction of 1,1-diphenylethane with hydrogen according to the method of the present invention, proceeds according to the reaction equation [I], based on the gas analysis of reaction products.

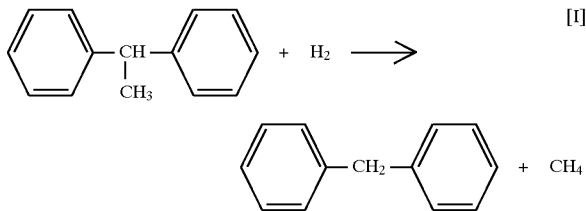

Furthermore, it is believed that the reaction of 1,1-diphenylethane with water proceeds according to the following reaction equation [II]. In addition, the reaction according to the equation (I) also proceeds due to the presence of hydrogen produced in the reaction [II] with water.

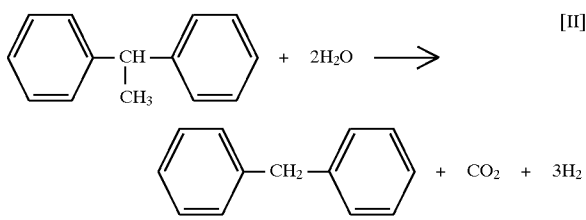

The ratios of feed components of 1,1-diphenylethane and hydrogen or water or their mixture, is so selected that the sum of hydrogen and water is generally in the range of about 1 to 30 moles relative to 1 mole of 1,1-diphenylethane. When the molar ratio of the sum of hydrogen and water is less than 1, the conversion rate tends to become and side reactions tend to occur. On the other hand, if the molar ratio exceeds 30, the conversion rate does not increase significantly with an increased amount of water or hydrogen, so that it is not economically desirable.

The reaction temperature is preferably in the range of 250° C. to 700° C. If the reaction temperature is lower than 250° C., the reaction rate is extremely low. On the other hand, when the temperature is higher than 700° C., side reactions such as decomposition occur at an undesirable level. The reaction pressure can be selected arbitrarily in the range of atmospheric pressure to a high pressure such as 100 kg/cm$^2$. It is preferable that the pressure and temperature are so selected that the reaction system is maintained in the phase.

It is desirable that the reaction is carried out in the presence of a metal catalyst of metal, metal oxide catalyst or mixtures thereof. The metal oxide preferably has basic to weak acidic property.

As the catalysts, various metals and metal oxides can be used. The metal catalysts are exemplified by the metals of Co, Rh, Ir, Ni, Pd, Pt, Re and Ru or mixtures thereof. Noble metal catalysts are preferred. More particularly, a metal catalyst containing Rh or Pd or both of them is more preferable. When a metal catalyst is used, the metal catalyst may be supported on basic to weak acidic carriers such as SiO$_2$, TiO$_2$ or Al$_2$O$_3$ procedures known in the art. The amount of a catalyst supported on the carrier is preferably in the range of 0.001–10% by weight.

The metal oxide catalysts are exemplified by CoO, BeO, NiO, CaO, $Na_2O$, $K_2O$, $UO_3$, $Cr_2O_3$, $Fe_2O_3$, $SiO_2$, $TiO_2$ and $Al_2O_3$ and mixtures thereof. Oxides of alkali metals and alkaline earth metals or their mixtures are preferred. Furthermore, the catalyst containing a oxides of Na or Ca or their mixture, is most preferred.

When a catalyst is used in the method of the present invention, the strongly acidic solid catalysts such as silica-alumina and zeolite are not preferred because they induce significant decomposition reactions even in the presence of hydrogen or water or their mixture.

In the process of the present invention, the mode of reaction may be either batch-wise or continuous process. In the continuous operation, any of fixed-bed system and fluidized-bed systems can be employed, in which the reaction is carried out by feeding 1,1-diphenylethane and water or hydrogen or their mixture into a reactor that is maintained at a prescribed temperature and pressure. The liquid space velocity of the feed of 1,1-diphenylethane can be selected in the range from 0.1 to 50 $hr^{-1}$. In the continuous process, it is generally desirable to recover the reacted mixture by allowing it to condense using a cold trap that is connected to an outlet of a reactor.

BEST MODE FOR CARRYING OUT THE INVENTION

The present invention will now be described in more detail with reference to several examples.

In the following examples, the reactions were carried out using the method, in which a certain amount of reactants were continuously fed into a reaction tube of 25 mm in inner diameter made of stainless steel, which was equipped with a heating device and was filled with 30 ml of catalyst.

The identification of the reaction products was done by mass spectrometry and the quantitative analysis was done by gas chromatography using a device with a 50 m capillary column (OV-1).

In the following examples, the feed rates of liquid 1,1-diphenylethane and water are given in ml/hr at room temperature, and the feed rate of gaseous hydrogen, is in ml/min terms of NTP.

EXAMPLE 1

Commercially available 0.5 wt. % Rh/alumina pellets (made by N. E. Chemcat Corporation) were crushed to make the particle size in the range of 0.35 to 1 mm and were filled into a reaction tube. At a temperature of 451° C. and a pressure of 1 atm, 1,1-diphenylethane (DPE) and hydrogen were fed into the reaction tube at flow rates of 30 ml/hr and 370 ml/min, respectively.

The liquid reaction products recovered in the cold trap were analyzed. The yield of diphenylmethane is shown in the following Table 1.

EXAMPLE 2

Commercially available 0.5 wt. % Rh/alumina pellets (made by N. E. Chemcat Corporation) were crushed and filled into a reaction tube in the like manner as in Example 1. At a temperature of 504° C. and a pressure of 12 atm, 1,1-diphenylethane and water were fed into the reaction tube at flow rates of 29.2 ml/hr and 24.0 ml/hr, respectively.

The liquid reaction products except water which were recovered in the cold trap were analyzed. The yield of diphenylmethane is shown in the following Table 1.

EXAMPLE 3

Commercially available 10 wt. % $Na_2O$/alumina pellets (made by Nissan Girdler Catalyst Co., Ltd.; trade name: G-92) were crushed and filled into a reaction tube in the like manner as in Example 1. At a temperature of 648° C. and at a pressure of 1 atm, 1,1-diphenylethane and water were fed into the reaction tube at flow rates of 30 ml/hr and 17.5 ml/hr, respectively.

The reaction products were obtained by cooling the outlet of the reaction tube with water. They recovered reaction products subjected to analysis. The yield of diphenylmethane is shown in the following Table 1.

EXAMPLE 4

Commercially available silica-calcia (silica-calcium oxide, made by Nikki Chemical Co., Ltd.; $SiO_2$/CaO=64/24 (wt. %); trade name: N-661B) were crashed to make the particle size in the range of 0.35 to 1.5 mm and was filled into a reaction tube. At a temperature of 598° C. and at a pressure of 1 atm, 1,1-diphenylethane and hydrogen were fed into the reaction tube at flow rates of 30 ml/hr and 370 ml/min, respectively.

The reaction products recovered from the cold trap were analyzed. The yield of diphenylmethane is shown in the following Table 1.

EXAMPLE 5

0.5 wt. % of Pd was supported on silica-calcia used in Example 4. This catalyst were crushed to make the particle size in the range of 0.35 to 1.5 mm and it was filled into a reaction tube. At a temperature of 600° C. and at a pressure of 11 atm, 1,1-diphenylethane and hydrogen were fed into the reaction tube at flow rates of 30.5 ml/hr and 140 ml/min, respectively.

The results of the reaction are shown in the following Table 1.

COMPARATIVE EXAMPLES 1, 2 AND 3

Tests were carried out employing the apparatus used in Example 1. In Comparative Example 1, the reaction was carried out without any catalyst, while in Comparative Examples 2 and 3, commercially available silica-alumina catalyst was used. By feeding neither water nor hydrogen, the reaction was carried out in the like manner as in Example 1 by feeding 1,1-diphenylethane.

The results are shown in the following Table 1 together with the reaction conditions.

TABLE 1

| Example | Catalyst | Reaction Condition Temperature (°C.) | Pressure (atm) | Flow Rate DPE (ml/hr) | Water (ml/hr) | Hydrogen (ml/min) | Yield of Diphenyl- methane (%) |
|---|---|---|---|---|---|---|---|
| Exam. 1 | 0.5 wt. % Rh/alumina pellets *1 | 451 | 1 | 30 | — | 370 | 10 |
| Exam. 2 | 0.5 wt. % Rh/alumina pellets *1 | 504 | 12 | 29.2 | 24 | — | 14 |
| Exam. 3 | Na$_2$O/Al$_2$O$_3$ *2 | 648 | 1 | 30 | 17.5 | — | 20 |
| Exam. 4 | Silica-calcia *3 | 598 | 1 | 30 | — | 370 | 9 |
| Exam. 5 | 0.5 wt. % Pd on silica-calcia *3 | 600 | 11 | 30.5 | — | 140 | 43 |
| Comp. Exam. 1 | Without catalyst | 600 | 1 | 30.5 | — | — | 3 |
| Comp. Exam. 2 | Comm. available silica-alumina | 600 | 1 | 30.5 | — | — | 3 |
| Comp. Exam. 3 | Comm. available silica-alumina | 500 | 1 | 30.5 | — | — | 0 |

Notes:
*1 0.5 wt. % Rh/alumina pellets: A catalyst made by N. E. Chemcat Corporation
*2 Na$_2$O/Al$_2$O$_3$: A catalyst made by Nissan Girdler Catalyst Co., Ltd.; trade name: G-92
*3 Silica-calcia: A catalyst made by Nikki Chemical Co., Ltd.; trade name: N-661B

ADVANTAGES OF THE INVENTION

According to the method of the present invention, it is possible to produce diphenylmethane as the major reaction product by reacting 1,1-diphenylethane with hydrogen or water, while minimizing side reactions such as hydrogenolysis to form benzene and ethylbenzene, dehydrogenation to form 1,1-diphenylethylene and decomposition to form styrene.

What is claimed is:

1. A method for producing diphenylmethane comprising reacting 1,1'-diphenylethane with hydrogen and/or water wherein the amount of hydrogen and/or water is from about 1 to about 30 moles relative to one mole of 1,1'-diphenylethane and the reaction temperature is from 250° C. to 700° C.

2. The method for producing diphenylmethane as claimed in claim 1, wherein the 1,1'-diphenylethane is reacted in the presence of at least one catalyst selected from the group consisting of metal catalysts and metal oxide catalysts.

3. The method for producing diphenylmethane as claimed in claim 2, wherein said catalyst is a metal catalyst comprising at least one member selected from the group consisting of Co, Rh, Ir, Ni, Pd, Pt, Re, and Ru.

4. The method for producing diphenylmethane as claimed in claim 2, wherein said catalyst is at least one noble metal.

5. The method for producing diphenylmethane as claimed in claim 2, wherein said catalyst is a metal oxide catalyst comprising at least one member selected from the group consisting of CoO, BeO, NiO, CaO, Na$_2$O, K$_2$O, UO$_3$, Cr$_2$O$_3$, Fe$_2$O$_3$, SiO$_2$, TiO$_2$, and Al$_2$O$_3$.

6. The method for producing diphenylmethane as claimed in claim 2, wherein said catalyst is a metal oxide catalyst comprising an alkali metal oxide and/or alkaline earth metal oxide.

7. The method for producing diphenylmethane as claimed in claim 2, wherein said catalyst is a metal oxide catalyst comprising sodium oxide and/or calcium oxide.

8. The method for producing diphenylmethane as claimed in claim 1, wherein 1,1'-diphenylethane is reacted with hydrogen.

9. The method for producing diphenylmethane as claimed in claim 2, wherein 1,1'-diphenylethane is reacted with hydrogen.

10. The method for producing diphenylmethane as claimed in claim 1, wherein 1,1'-diphenylethane is reacted with water.

11. The method for producing diphenylmethane as claimed in claim 2, comprising reacting of 1,1'-diphenylethane with water.

12. The method for producing diphenylmethane as claimed in claim 1, wherein 1,1'-diphenylethane is reacted with mixture of hydrogen and water.

13. The method for producing diphenylmethane as claimed in claim 2, wherein 1,1'-diphenylethane is reacted with a mixture of hydrogen and water.

14. The method for producing diphenylmethane as claimed in claim 1, wherein the reaction pressure is in the range from atmospheric pressure to about 100 kg/cm$^2$.

15. The method for producing diphenylmethane as claimed in claim 1, wherein the starting material is a hydrocarbon oil comprising at least about 50 % by weight of 1,1'-diphenylethane.

16. The method for producing diphenylmethane as claimed in claim 1, wherein the yield of diphenylmethane is at least about 9%.

* * * * *